(12) United States Patent
Nachtomy et al.

(10) Patent No.: US 12,048,494 B2
(45) Date of Patent: Jul. 30, 2024

(54) NAVIGATING BRONCHIAL PATHWAYS

(71) Applicant: KONINKLIJKE PHILIPS N.V., Eindhoven (NL)

(72) Inventors: Ehud Nachtomy, Herzliya (IL); Erik Van Der Heijden, Nijmegen (NL); Roel Verhoeven, Arnhem (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 100 days.

(21) Appl. No.: 17/786,052

(22) PCT Filed: Dec. 11, 2020

(86) PCT No.: PCT/EP2020/085661
§ 371 (c)(1),
(2) Date: Jun. 16, 2022

(87) PCT Pub. No.: WO2021/122344
PCT Pub. Date: Jun. 24, 2021

(65) Prior Publication Data
US 2023/0135733 A1    May 4, 2023

(30) Foreign Application Priority Data

Dec. 17, 2019  (EP) .................................... 19217043

(51) Int. Cl.
*A61B 34/20*   (2016.01)
*A61B 6/00*    (2006.01)
(Continued)

(52) U.S. Cl.
CPC .............. *A61B 34/20* (2016.02); *A61B 6/032* (2013.01); *A61B 6/4085* (2013.01);
(Continued)

(58) Field of Classification Search
CPC ....... A61B 34/20; A61B 6/032; A61B 6/4085; A61B 6/4417; A61B 6/463; A61B 6/466;
(Continued)

(56) References Cited

U.S. PATENT DOCUMENTS 6,580,938 B1 *  6/2003  Acker ................... A61B 5/062
                                                              600/429
7,697,972 B2     4/2010  Verard
(Continued)

FOREIGN PATENT DOCUMENTS

WO    2012117321 A1    9/2012
WO    2018215832 A2   11/2018

OTHER PUBLICATIONS

International Search Report and Written Opinion of PCT/EP2020/085661, dated Feb. 21, 2021.
(Continued)

*Primary Examiner* — Dixomara Vargas

(57) ABSTRACT

The present invention relates to navigating in bronchial pathways. In order to provide further improved navigation guidance, a sequence of 2D X-ray images of a region of interest of a bronchial structure with an intrathoracic device (visible in the X-ray images) inserted in a bronchial pathway is provided. The intrathoracic device is tracked in the 2D X-ray images and direction and magnitude of repetitory cardiovascular and respiratory induced motion is assessed based on the tracked intrathoracic device. The assessed motion is modelled and a navigation information indicative of a range of the modelled motion is generated. The navigation information is shown as a confidence reference (310), for example a rEBUS historical trajectory confidence reference, to a user operating the intrathoracic device. As an example, an augmented fluoroscopy 2D image (302) of a thorax region is registered and shown overlaid with segmentation (304) of the bronchial structure and target lesion
(Continued)

(312). Further, a confidence reference (314) of the current position of the rEBUS catheter may also be shown.

15 Claims, 4 Drawing Sheets

(51) Int. Cl.

| | | |
|---|---|---|
| *A61B 6/03* | (2006.01) | |
| *A61B 6/40* | (2024.01) | |
| *A61B 6/46* | (2024.01) | |
| *A61B 6/50* | (2024.01) | |
| *A61B 8/12* | (2006.01) | |
| *A61B 10/02* | (2006.01) | |
| *G06T 7/11* | (2017.01) | |
| *G06T 7/30* | (2017.01) | |
| *A61B 34/10* | (2016.01) | |
| *A61B 90/00* | (2016.01) | |

(52) U.S. Cl.
CPC ............ *A61B 6/4417* (2013.01); *A61B 6/463* (2013.01); *A61B 6/466* (2013.01); *A61B 6/50* (2013.01); *A61B 6/5247* (2013.01); *A61B 6/5264* (2013.01); *A61B 8/12* (2013.01); *A61B 10/02* (2013.01); *G06T 7/11* (2017.01); *G06T 7/30* (2017.01); *A61B 2034/107* (2016.02); *A61B 2034/2051* (2016.02); *A61B 2034/2065* (2016.02); *A61B 2090/3966* (2016.02); *G06T 2207/10081* (2013.01); *G06T 2207/10132* (2013.01); *G06T 2207/30061* (2013.01)

(58) Field of Classification Search
CPC ....... A61B 6/50; A61B 6/5247; A61B 6/5264; A61B 8/12; A61B 10/02; A61B 2034/107; A61B 2034/2051; G06T 7/11; G06T 7/30

See application file for complete search history.

(56) References Cited

U.S. PATENT DOCUMENTS

| | | | |
|---|---|---|---|
| 9,044,254 B2 | 6/2015 | Ladtkow | |
| 2008/0177280 A1* | 7/2008 | Adler | A61B 90/10 |
| | | | 901/41 |
| 2013/0071001 A1 | 3/2013 | Waechter-Stehle | |
| 2015/0265368 A1* | 9/2015 | Chopra | A61B 1/000094 |
| | | | 600/587 |
| 2018/0078195 A1* | 3/2018 | Sutaria | A61B 5/065 |
| 2018/0256262 A1* | 9/2018 | Duindam | A61B 1/005 |
| 2019/0038365 A1* | 2/2019 | Soper | G06T 7/80 |
| 2019/0350659 A1* | 11/2019 | Wang | A61B 8/0841 |
| 2019/0374130 A1 | 12/2019 | Bydlon | |
| 2019/0378329 A1* | 12/2019 | Kiely | A61B 6/5288 |
| 2020/0229679 A1* | 7/2020 | Zhao | A61B 34/20 |
| 2020/0242767 A1* | 7/2020 | Zhao | A61B 34/37 |
| 2021/0137634 A1* | 5/2021 | Lang | A61B 5/113 |
| 2022/0142714 A1* | 5/2022 | Soper | A61B 5/066 |
| 2023/0083936 A1* | 3/2023 | Benseghir | A61B 6/12 |
| | | | 600/424 |
| 2023/0157769 A1* | 5/2023 | Gadda | A61B 5/113 |
| | | | 606/130 |

OTHER PUBLICATIONS

Sorger, Hanne et al "A Multimodal Image Guiding System for Navigated Ultrasound Bronchoscopy (EBUS): A Human Feasibility Study", PLOS ONE, Feb. 2017, pp. 1-15.

Lessman, Nikolas et al, "Feasibility of Respiratory Motion-Compensated Stereoscopic X-Ray Tracking for Bronchoscopy", International Journal of Computer Assisted Radiology and Surgegy, vol. 9, No. 2, Jul. 2013, pp. 199-209.

MacMahon, Heber et al "Guidelines for Management of Incidental Pulmonary Nodules Detected on CT Images", Radiology, vol. 284, No. 1, Jul. 2017.

Rivera, M. Patricia et al Establishing the Diagnosis of Lung Cancer, Chest, 2013.

* cited by examiner

NAVIGATING BRONCHIAL PATHWAYS

CROSS-REFERENCE TO PRIOR APPLICATIONS

This application is the U.S. National Phase application under 35 U.S.C. § 371 of International Application No. PCT/EP2020/085661, filed on Dec. 11, 20209, which claims the benefit of European Patent Application No. 19217043.9, filed on Dec. 17, 2019. These applications are hereby incorporated by reference herein.

FIELD OF THE INVENTION

The present invention relates to endobronchial and transbronchial navigation of devices. The present invention relates in particular to a device for facilitating navigation of an intrathoracic device inside a bronchial pathway, to a system for navigation of an intrathoracic device inside a bronchial pathway and to a method for navigation of an intrathoracic device inside a bronchial pathway

BACKGROUND OF THE INVENTION

Peripheral pulmonary lesions (PPL) may be diagnosed by non-surgical biopsy. In an example workflow, the peripheral pulmonary nodule is localized and identified as needing further diagnosis by pre-operative CT scans. An example for an endobronchial approach to performing non-surgical biopsy is being minimally invasive. An example of endobronchial approaches is a fluoroscopy guided intrathoracic biopsy. Conventional fluoroscopy (i.e. X-ray based) is used to help and guide transbronchial navigation and biopsy in the diagnostics of peripheral pulmonary lesions. The endoscopist is then guided by 2D fluoroscopy for a coarse approximation of where the diagnostic tools and the to-be-diagnosed lesions should be, and how they are positioned relative to another. In another approach, an endobronchial ultrasound radial mini-probe (rEBUS) might be utilized to help guide the physician. rEBUS might be utilized alone or in combination with fluoroscopy. It is not necessarily a navigation method, but can provide valuable confirmatory information on if a lesion has been reached. Either one of approaches helps in further guiding accurate endobronchial biopsy. Combining them provides additive information, as 2D fluoroscopy can help guide coarse navigation and localization whilst rEBUS imaging can provide local confirmatory imaging. WO 2018 215832 A2 relates to methods for using radial endobronchial ultrasound probes for 3D REM construction of images and improved target localization. However, it has been shown that navigation can still become cumbersome for the operator.

SUMMARY OF THE INVENTION

There may thus be a need for further improved navigation guidance. The object of the present invention is solved by the subject-matter of the independent claims; further embodiments are incorporated in the dependent claims. It should be noted that the following described aspects of the invention apply for the device for facilitating navigation of an intrathoracic device inside a bronchial pathway, for the system for navigation of an intrathoracic device inside a bronchial pathway and for the method for navigation of an intrathoracic device inside a bronchial pathway.

According to the present invention, a device for facilitating navigation of an intrathoracic device inside a bronchial pathway is provided. The device comprises an image data provider, a processor and an output data provider. The image data provider is configured to receive a sequence of 2D X-ray images of the region of interest of the bronchial structure with a device inserted in a bronchial pathway. The intrathoracic device is visible in the X-ray images. The processor is configured to track the intrathoracic device in at least a part of the sequence of 2D X-ray images. The processor is also configured to assess direction and magnitude of repetitory cardiovascular and respiratory induced motion based on the tracked intrathoracic device. The processor is further configured to model the assessed motion and to generate a navigation information indicative of a range of the modelled motion. The output data provider is configured to provide the navigation information as a confidence reference to a user operating the intrathoracic device.

The term "bronchial pathway" relates to the lungs, for example, but also other parts of the pathway for breathing in and out.

The term "intrathoracic" relates to being within the thorax and relates to e.g. intrapulmonary, intrathoracic and also transthoracic. Also, the term comprises transbronchial. The intrathoracic device thus relates to an endobronchial or transbronchial device.

In an example, the processor is also configured to track an intrathoracic region of interest in at least a part of the sequence of 2D X-ray images.

In an example, the processor is configured to enable distinction of the repetitory motion from single event motion, such as induced by endobronchial or transbronchial device manipulation or any of its guiding elements.

In another example, the processor is further configured to enable modelling of found device positioning relative to a pre-procedural imaging source.

In an example, for motion modelling, in addition to following the device, information is provided how a bronchial tree actually looks like. The confidence interval positioning is related to pre-procedural knowledge of bronchial tree positioning.

In an option, the endobronchial device is tracked, then positioned at main carina, and image data is generated. Further, it is positioned at part of or all of the subcarinas of every pulmonary segment (e.g. right upper lobe, right middle lobe, right lower lobe, left upper lobe, left lower lobe), and image data is generated. Further, it is provided to register, e.g. automatically register, pre-procedural anatomical image to fluoroscopy images, as it is known how the pre-procedural segmentation of lungs would fit in the fluoroscopy images.

Fluoroscopy imaging is an X-ray imaging that is also referred to as fluoro imaging or fluoro.

In a further example, anatomical features such as the lungs are tracked based on features to increase the model's accuracy.

This provides essential information to the user when navigating, which hence means relief and improvement in navigation of bronchial and lung structures. The indication of a possible space in which the device, like an imaging probe or an extractor, is located provides guidance for the operator in an intuitive way.

In an example, coarse features in the intrathoracic region of interest are taking into account in order to be able to give an 'error' or adjust the confidence interval if a dislocation of the coarser pulmonary features is detected. This is for example the case when a catheter is rotated with predefined (passive) angulation. The lung segment or lesion can be seen to move as the catheter rotates.

In an example, the image data provider is configured to receive pre-procedural imaging information of the patient, i.e. PET-CT, CT (or a variation thereof, i.e. cone beam CT) and/or MRI.

According to an example, the confidence reference is provided as an indication of an envelope enclosing the spatial range of the modelled motion.

According to an example, the processor is configured to track the intrathoracic device in at least a part of the sequence of 2D X-ray images; and to assess direction and magnitude of non-repetitory lung tissue and device motion as induced by intrathoracic device manipulation or its guiding elements, i.e. endoscope; and to track the motion and generating a navigation information which is adjusted for the non-repetitory motion induced by endobronchial or transbronchial device manipulating or its guiding elements.

According to an example, the image data provider is further configured to provide pre-operative 3D image data comprising a segmented bronchial structure of the subject in the region of interest. The processor is configured to register the 2D X-ray images with the pre-operative 3D image data. The processor is further configured to determine a spatial position of the intrathoracic device in relation to the segmented bronchial structure of the pre-operative 3D image data based on the 2D X-ray projection of the transthoracic device. The output data provider comprises a display that is configured to display the confidence reference in a projection of the segmented bronchial structure, which are both overlaid to a current one of the sequences of 2D X-ray images.

According to an example, the image data provider is further configured to provide 3D (reconstructed) image data originating from intra operative X-ray fluoroscopy such as Cone beam computed tomography and, as an option, further comprising a segmented bronchial structure of the subject in the region of interest. The processor is configured to register the 2D X-ray images with the (reconstructed) 3D image data. The processor is also configured to determine a spatial position of the transthoracic device in relation to the segmented bronchial structure of the 3D image data based on the 2D X-ray projection of the transthoracic device. The output data provider comprises a display that is configured to display the confidence reference overlaid in 3D form on the display of the 3D image data.

In an example, the image data is originating from a sweep of a C-arm acquiring at least multiple projections under multiple different angles, possibly further providing a segmented bronchial structure of the subject, such as a patient, or 3D tool location in the region of interest.

According to an example, the image data provider is configured to receive, as the sequence, a live stream of 2D X-ray images. The processor is configured to continuously track the intrathoracic device in the images. The processor is further configured to update the navigation information accordingly. The output data provider is configured to continuously provide the navigation information as an updated confidence reference to a user operating the intrathoracic device.

According to an example, the X-ray information is further updated and/or integrated with electromagnetic tracking information.

In an example, an offline operation from X-ray is provided by using electromagnetic navigation. In another example, passive impedance based localization of intrathoracic devices is used.

According to the present invention, also a system for navigation of an intrathoracic device inside a bronchial pathway is provided. The system comprises an X-ray imaging device for imaging a thorax area of interest of a subject and an intrathoracic device for insertion in a bronchial pathway, such as the lungs of a subject. The system also comprises a display and a device for facilitating navigation according to one of the preceding examples. The intrathoracic device is at least partly radio-opaque. The X-ray imaging device provides a sequence of 2D X-ray images of the region of interest of the bronchial structure with the intrathoracic device inserted in the bronchial pathway. The output data provider provides the navigation information, i.e. the visual indication, to the display. In an example, the display is a monitor or display as used by the operator. The display provides at least one of the sequences of the 2D X-ray images and the visual indication as a confidence reference overlaid to the 2D X-ray image.

According to an example, the intrathoracic device is an ultrasound imaging probe configured to provide radial endobronchial ultrasonography data from within bronchial structure, e.g. the lungs.

In an example, the intrathoracic device is an ultrasound imaging probe configured to provide radial and/or forward looking endobronchial ultrasonography data from within a bronchial structure.

In an example, the intrathoracic device is an endobronchial ultrasound device, also referred to as EBUS. The device may be configured for radial and/or forward looking ultrasound imaging.

In another example, the intrathoracic device is an endobronchial ultrasound mini probe, i.e. radial endobronchial ultrasound mini device or forward looking endobronchial ultrasound mini device. The device may be configured for radial and/or forward looking ultrasound imaging.

In the following, when EBUS is referred to, also rEBUS is provided, and vice versa.

According to an example, the intrathoracic device comprises an ultrasound imaging probe and a tissue or cell extraction device. In an example, the tissue or cell extraction device is a biopsy device.

This provides further improvement in biopsy of for example peripheral pulmonary lesions, in addition to navigation guidance towards same.

According to the present invention, also a method for navigation of an intrathoracic device inside a bronchial pathway is provided. The method comprises the following steps:

Receiving a sequence of live 2D X-ray images of the region of interest of the bronchial structure with an intrathoracic device inserted in a bronchial pathway, the intrathoracic device being visible in the X-ray images;

Tracking the intrathoracic device in at least a part of the sequence of live 2D X-ray images;

Assessing direction and magnitude of repetitory cardiovascular and respiratory induced motion based on the tracked intrathoracic device;

Modeling the assessed motion and generating a navigation information indicative of the modelled motion; and Providing the navigation information as a confidence reference to a user operating the intrathoracic device.

According to an aspect of the present invention, potential and/or existing device radio-opaque properties are used for automated tracking under fluoroscopy in bronchoscopy navigation for enhancing navigation of e.g. known catheters, devices and/or radial endobronchial ultrasonography devices to the lesion, providing lesion access confirmation and/or help guide biopsy extraction. For example, computer vision and image processing for 2D and/or 3D tracking of the catheter is deployed. Further, it is provided to augment fluoroscopy images and to display with the results of device tracking in 2D and/or 3D. In another example, results of device tracking in 2D/3D are registered with results of pre-procedural computed tomography (CT) planning, 2D fluoroscopy under multiple angles (continuously or at distinct angles) and/or cone beam CT scans and/or electromagnetic navigation bronchoscopy. In an example, a minimum of 30° wide sweep under continuous fluoroscopy is provided to have a 3D update of lesion and device positioning. In another example, a minimum of less than a 30° wide sweep is provided, such as a 20° wide sweep.

According to an aspect of the present invention, the present invention relates to navigating endo- or transbronchially. For example, the navigation relates to navigating in bronchial pathways. In order to provide further improved navigation guidance, a sequence of 2D X-ray images of a region of interest of a bronchial structure with an intrathoracic device (visible in the X-ray images) inserted in a bronchial pathway is provided. The intrathoracic device is tracked in the 2D X-ray images and direction and magnitude of repetitory cardiovascular and respiratory induced motion is assessed based on the tracked intrathoracic device. The assessed motion is modelled and a navigation information indicative of the range of modelled motion is generated. The navigation information of potential device positioning is presented to the operator, for example an EBUS or rEBUS historical trajectory confidence reference, to a user operating the intrathoracic device. As an example, an X-ray 2D image of a thorax region is registered and shown overlaid with a static segmentation of the bronchial structure derived from use of cone beam CT, i.e. cone beam fluoroscopy in case of X-ray imaging (i.e. with a C-arm system) normally in combination with pre-operative CT. As an example, an augmented fluoroscopy 2D image (302) of a thorax region is registered and shown overlaid with segmentation (304) of the bronchial structure and target lesion (312). Further, a confidence reference (314) of the current position of the rEBUS catheter may also be shown.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
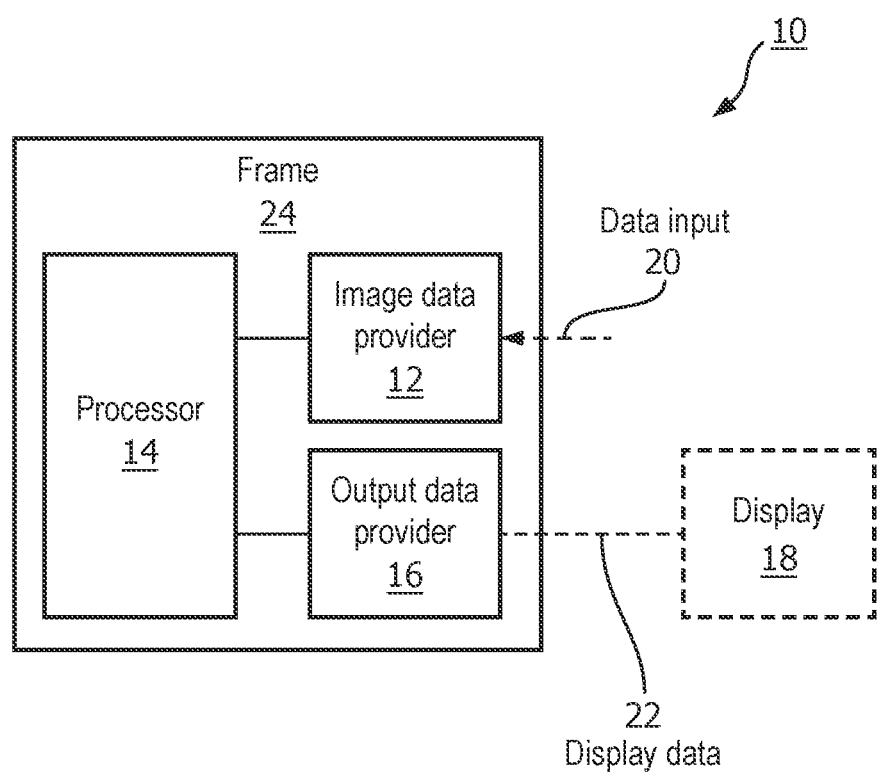
FIG. 1 schematically shows a device for facilitating navigation of an intrathoracic device inside a bronchial pathway.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

The term "subject" may also be referred to as individual. The subject may further also be referred to as patient, although it is noted that this term does not indicate whether any illness or disease is actually present with the subject.

FIG. 1 schematically shows a device 10 for facilitating navigation of an intrathoracic device inside a bronchial pathway. The device 10 for facilitating navigation comprises an image data provider 12, a processor 14 and an output data provider 16. The image data provider 12 is configured to receive a sequence of 2D X-ray images of the region of interest of the bronchial structure with an intrathoracic device inserted in a bronchial pathway. The intrathoracic device is visible in the X-ray images. The processor 14 is configured to track the intrathoracic device in at least a part of the sequence of 2D X-ray images; to assess direction and magnitude of repetitory cardiovascular and respiratory induced motion based on the tracked intrathoracic device; and to model the assessed motion and generating a navigation information indicative of a range of the modelled motion. The output data provider 16 is configured to provide the navigation information as a confidence reference to a user operating the intrathoracic device.

The "device for facilitating navigation" is also referred to as "navigation device". The "output data provider" is also referred to as "navigation facilitator". The "navigation information indicative of a range of the modelled motion" is also referred to as "visual indicator of a range of the modelled motion".

In an example, the sequence of images is a sequence of live images.

The assessed motion can also be referred to as estimated range of motion.

It is noted that e.g. repetitory tissue motion induced by cardiovascular and respiratory movement may result in up to several cm tissue motion.

In an example, the intrathoracic device is an ultrasound imaging probe that provides radial endobronchial ultrasonography data from within the bronchial structure.

For tracking the intrathoracic device, three radio-opaque markers are provided in a predetermined spatial arrangement along the intrathoracic device. Thus, the location, position and orientation can be tracked based on the X-ray radiation images.

By tracking the intrathoracic device, a plane can be identified to be shown on or overlaid to the X-ray images such as fluoroscopic images.

In an example, the location of the intrathoracic device is registered with the X-ray images. In an example, the tip of the intrathoracic device along with radio-opaque markers are used for registering. The intrathoracic device is thus registered within the subject's anatomy.

The confidence reference replaces a dynamic model of the anatomy. The confidence reference can also be referred to as confidence map.

In an option, not further shown in detail, the confidence reference is provided as an indication of an envelope enclosing the spatial range of the modelled motion.

In an example, the confidence reference is provided as an indication of an envelope enclosing the spatial range of the modelled motion in relation to the target, e.g. the target lesion and/or the current location of the catheter, or trajectory of the catheter.

As an example, the confidence reference is shown overlaid to a fluoroscopy image.

In another example, the confidence reference is provided as an indication of an envelope enclosing the spatial range of the modelled motion in relation to the subject. In a further example, the confidence reference is provided as an indication of an envelope enclosing the spatial range of the modelled motion in relation to a segmented object such as lesion overlaid to the fluoroscopy image.

The range of motion is thus also displayed in relation to the X-ray imaging such as fluoroscopy images. In an example, the range of motion is provided as a motion envelope.

In example, shown as an option with dashed lines in FIG. 1, the output data provider 16 comprises a display 18 that is configured to display the confidence reference overlaid to a current one of the sequences of 2D X-ray images. The display 18 is data-connected to the output data provider 16, as indicated with a dashed connection line 22.

A first arrow 20 is shown in dashed lines to indicate a data input to the image data provider 12. For example, a data connection to an imaging system may be provided, e.g. wireless or as wire connection.

As an option, a frame 24 indicates an integration of the data provider 12, the processor 14 and the output data provider 16. For example, they are provided in a common housing. In another example, they are combined and integrated as separate modules.

In another example, they are provided independently from each other, being data connected, though.

The current one of the sequences of 2D X-ray images can also be referred to as live image.

In an example, the 2D X-ray images are provided from a C-arm in a single imaging positioning. In another example, the 2D X-ray images are provided from a C-arm in multiple imaging positionings.

In an example, the image data provider 12 is further configured to provide pre-operative 3D image data comprising a segmented bronchial structure of the subject in a region of interest. The processor 14 is configured to register the 2D X-ray images with the pre-operative 3D image data; and to determine a spatial position of the intrathoracic device in relation to the segmented bronchial structure of the pre-operative 3D image data based on the 2D X-ray projection of the intrathoracic device. The output data provider 16 comprises the display 18 that is configured to display the confidence reference in a projection of the segmented bronchial structure, which are both overlaid to a current one of the sequence of 2D X-ray images. In an example, a consistent position of the 2D X-ray projection is provided, or a moving sweep from which a 3D reconstruction is made.

In an example, the image data provider 12 is further configured to provide 3D image data originating from intra operative X-ray fluoroscopy such as cone beam computed tomography comprising a segmented bronchial structure of the subject in the region of interest. The processor 14 is configured to register the 2D X-ray images with the 3D image data; and to determine a spatial position of the intrathoracic device in relation to the segmented bronchial structure of the 3D image data based on the 2D X-ray projection of the intrathoracic device. The output data provider 16 comprises the display 18 that is configured to display the confidence reference overlaid in 3D form on the display of the 3D image data.

Cone beam computed tomography is also referred to as cone beam CT, CBCT or cbCT.

In an example, the fluoroscopy images are augmented by the pre-operative 3D CT image data.

In an example, the image data provider 12 is configured to receive, as the sequence, a live stream of the 2D X-ray images. The processor 14 is configured to continuously track the intrathoracic device; and to update the navigation information accordingly. The output data provider 16 is configured to continuously provide the navigation information as an updated confidence reference to a user operating the intrathoracic device.

In an example, a single consistent position is provided for the sequence, i.e. the live stream of the 2D X-ray images.

In an example, a multi-X-ray positioning is provided. The term "continuously" relates to a rate of a number of tracking steps per second such that in the user's experience, a real-time tracking is provided.

The term "operator" refers to a person operating the device for facilitating navigation. For example, the operator is a technician, a physician assistance, a staff member, a nurse, a physician or the like.

Figure 2:
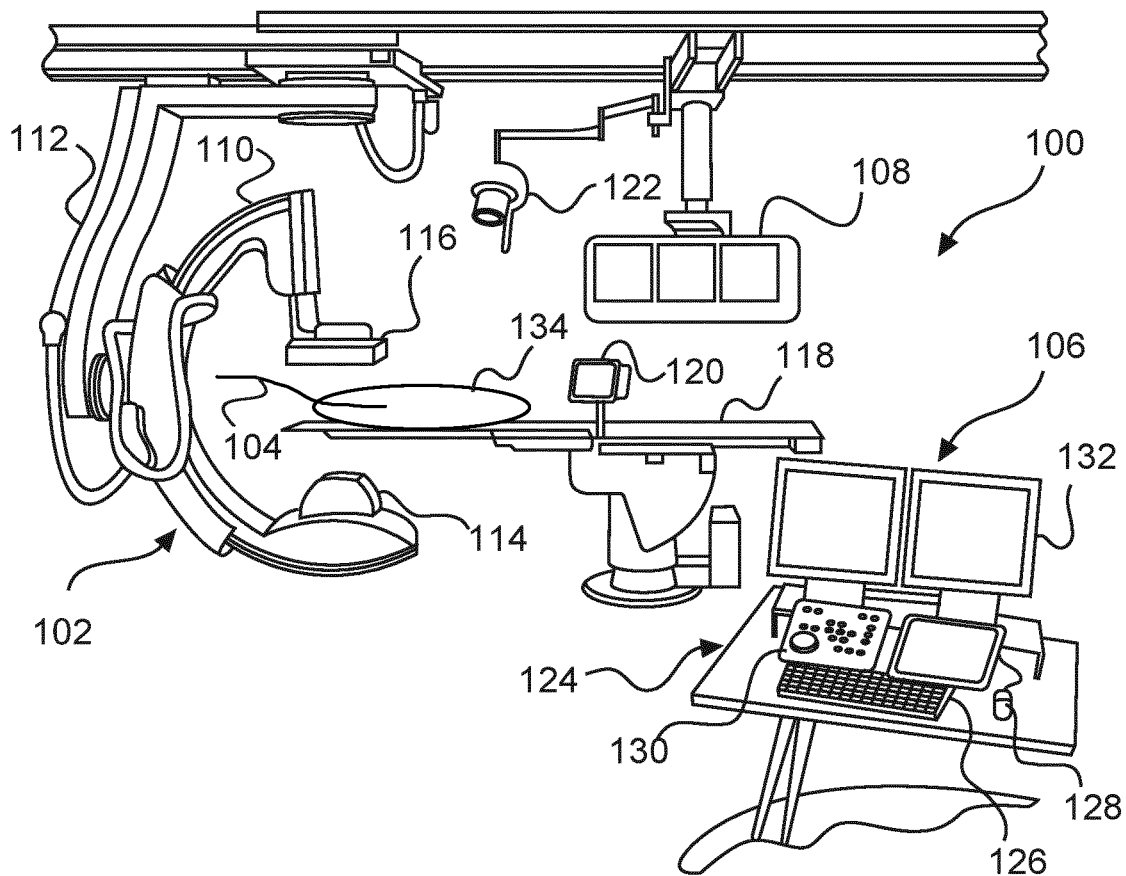
FIG. 2 shows an example of a system for navigation of an intrathoracic device inside a bronchial pathway.

FIG. 2 shows an example of a system 100 for navigation of an intrathoracic device inside a bronchial pathway. The system 100 comprises an X-ray imaging device 102 for imaging a thorax area of interest of a subject. The system 100 also comprises an intrathoracic device 104 for insertion in a bronchial pathway of a subject. Still further, the system 100 comprises a device 106 for facilitating navigation according to one of the preceding examples and a display 108. The intrathoracic device 104 is at least partly radio-opaque. The X-ray imaging device 102 provides a sequence of 2D X-ray images of the region of interest of the bronchial structure with the intrathoracic device 104 inserted in the bronchial pathway. The device 106 for facilitating navigation provides the navigation information to the display 108. The display 108 provides at least one of the sequences of the 2D X-ray images and the navigation information as a confidence reference overlaid to the 2D X-ray image.

The term radio-opaque refers to at least partly opacity for X-ray radiation. Briefly said, the term refers to being visible e.g. in (X-ray) fluoroscopic images.

As an example, the X-ray imaging device 102 is provided as a C-arm structure with a C-arm 110 mounted to a movable ceiling support 112. An X-ray source 114 and an X-ray detector 116 are provided at opposing ends of the C-arm 110.

A subject support 118 is provided, e.g. a patient table. A table-side display and interface module 120 may be arranged. Further, adjustable lighting 122 is provided above. The device 106 for facilitating navigation is provided as a control station 124, e.g. arranged sideward. The control station 124 comprises display and interface components such as a keyboard 126, a mouse 128, a control panel 130 and display units 132, to allow operation and control of the multiple equipment, e.g. in the examination room or intervention room or operation room.

Figure 4:
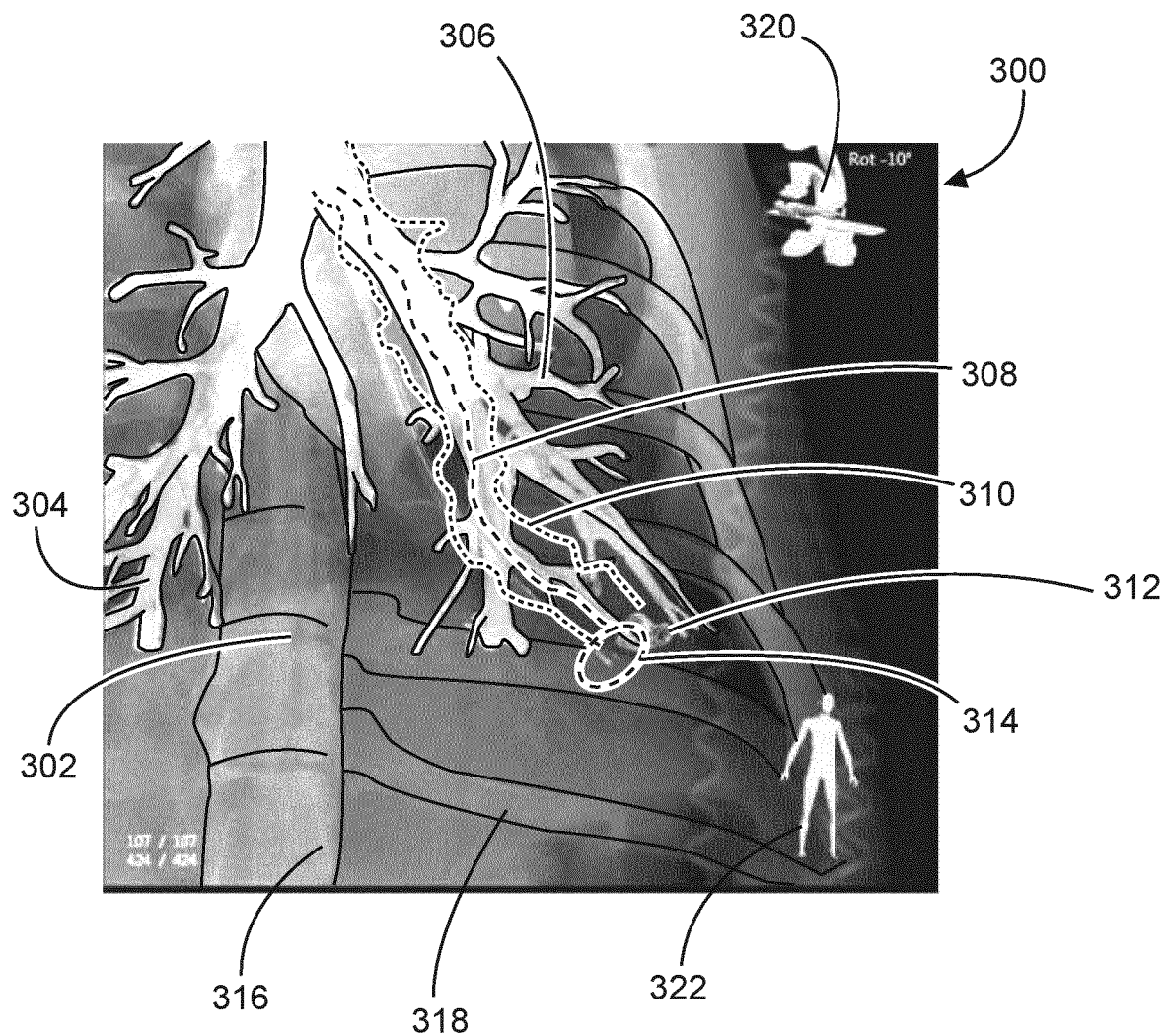
FIG. 4 schematically shows an example of an augmented live fluoroscopy 2D image of a thorax region with a confidence reference overlaid to the 2D X-ray image around the current catheter position.

A subject 134 may be arranged on the subject support 118. The intrathoracic device 104, e.g. an ultrasound imaging probe or an extraction device, may be inserted into the bronchial pathway of the subject 134 (not shown in detail). The X-ray imaging device 102 provides image data about the situation inside the subject, i.e. inside the body of the subject, which situation is not visible for the operator from outside. The image data is provided on the display 108, e.g. as fluoroscopic images, such as shown in FIG. 4.

In an example, the X-ray imaging device 102 is configured to provide the sequence of 2D X-ray images of the region of interest of the bronchial structure with the intrathoracic device inserted in the bronchial pathway to the device for facilitating navigation. The device 106 for facilitating navigation is configured to provide the navigation information to the display 108. The display 108 is configured to provide at least one of the sequences of the 2D X-ray images and the navigation information as a confidence reference overlaid to the 2D X-ray image.

As an example, distinct and spaced X-ray radiation opaque markers on the intrathoracic device 104, like an imaging probe's catheter, may be provided, to be automatically and continuously tracked under fluoroscopy by computer vision. For example, a catheter is used for pulmonary purposes that is visible under fluoroscopy through appearance of three markers, e.g. 10 mm apart from each other, and an ultrasound transducer located distally at a fixed distance from the markers may also be X-ray radiation opaque, i.e. radio-opaque.

Computer vision can then recognize the RO signature of the catheter and track its movement automatically both in 2D and potentially in 3D thus also providing spatial location and orientation.

In an option, the intrathoracic device 104 is an ultrasound imaging probe configured to provide radial endobronchial ultrasonography data from within a bronchial structure.

Endobronchial ultrasonography is also referred to as EBUS; as indicated above, radial endobronchial ultrasonography is referred to as rEBUS, REBUS or R-EBUS. In an example, a miniature ultrasound probe, e.g. an EBUS or radial EBUS probe, is inserted through a working channel of a flexible bronchoscope or catheter, which is also referred to as guide sheath. By imaging the surrounding tissue, the staff, e.g. a clinician, can determine a lesion's location and size.

In an option, the radial endobronchial ultrasonography data from within the bronchial structure is visualized and also shown on the display 108.

In an example, the intrathoracic device 104 comprises an ultrasound imaging probe and a biopsy extraction device.

Figure 3:
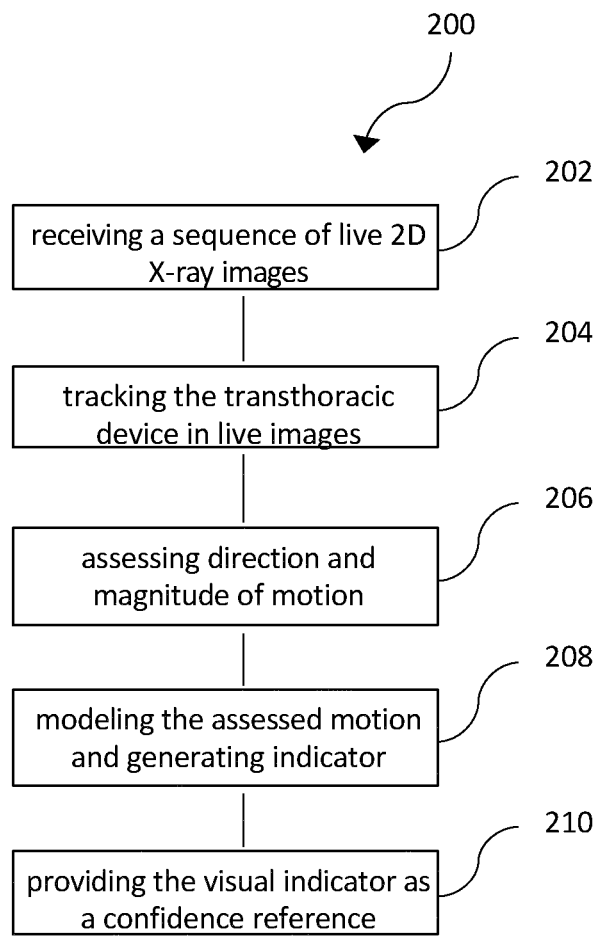
FIG. 3 schematically shows basic steps of a method for navigation of an intrathoracic device inside a bronchial pathway.

FIG. 3 schematically shows basic steps of a method 200 for navigation of an intrathoracic device inside a bronchial pathway. The method 200 comprises the following steps:

In a first step 202, also referred to as step a), a sequence of live 2D X-ray images of the region of interest of the bronchial structure with an intrathoracic device inserted in a bronchial pathway is received. The intrathoracic device is visible in the X-ray images.

In a second step 204, also referred to as step b), the intrathoracic device is tracked in at least a part of the sequence of live 2D X-ray images.

In a third step 206, also referred to as step c), direction and magnitude of repetitory cardiovascular and respiratory induced motion are assessed based on the tracked intrathoracic device.

In a fourth step 208, also referred to as step d), the assessed motion is modelled, and a navigation information indicative of the modelled motion is generated.

In a fifth step 210, also referred to as step e), the navigation information is provided as a confidence reference to a user operating the intrathoracic device.

In an example, not further shown in detail, it is further provided the steps of:

providing pre-operative 3D image data comprising a segmented bronchial structure of the subject in the region of interest;

registering the live 2D X-ray images with the pre-operative 3D image data;

determining a spatial position of the intrathoracic device in relation to the segmented bronchial structure of the pre-operative 3D image data based on the 2D X-ray projection of the intrathoracic device; and displaying the confidence reference in a projection of the segmented bronchial structure overlaid to a live 2D X-ray image.

In another example, also not further shown in detail, it is provided the steps of:

providing 3D image data originating from intra operative X-ray fluoroscopy such as cone beam CT, comprising a segmented bronchial structure of the subject in the region of interest;

registering the live 2D X-ray images with the 3D image data;

determining a spatial position of the intrathoracic device in relation to the segmented bronchial structure of the 3D image data based on the 2D X-ray projection of the intrathoracic device; and displaying the confidence reference overlaid as a 3D form on the display of the 3D image data.

FIG. 4 schematically shows a display 300 of an augmented live fluoroscopy 2D image 302 of a thorax region with an overlaid segmented bronchial tree 304 and target lesion. The overlay 304 comprises a bronchial structure 306. A calculated EBUS/rEBUS pathway 308 after registration is indicated in a dashed line pattern. An EBUS/rEBUS historical trajectory confidence reference is shown as an example of the confidence reference 310. Further, a current position confidence reference 314 relating to the current position of the EBUS/rEBUS catheter is also shown. In this example, the confidence references are displayed as 2D overlays but in other examples can also be projected as 3D structures.

The augmented X-ray image, i.e. the fluoroscopy 2D image 302, shows an anatomical structure with slightly visible vertebras 316, ribs 318 and other structures.

The static overlay 304 is provided as segmented visualization of the bronchial structure 306 and target lesion 312. For an easier differentiation, the static overlay 304 may be provided colored in contrast to the more or less greyscale only X-ray image. Further, information about a current C-arm orientation 320 or a subject orientation indicator 322 can be shown overlaid.

FIG. 4 provides an augmented display of a live 2D Fluoroscopy image with a segmented bronchial pathway and a segmented target lesion derived from use of CbCT normally in combination with pre-operative CT and a rEBUS catheter with its transducer and radio-opaque markers. The confidence reference supports in navigating the rEBUS catheter to the target lesion, confirm its location and then e.g. perform biopsy samples with biopsy tools.

For example, based on automated tracking, the rEBUS radio-opaque markers and transducer, tissue motion confidence references in 2D and/or 3D, indicated in a dotted line can be established around the current presumed location of the ultrasound transducer and can further clarify to the operator from what spatial region the rEBUS imaging (not shown) may originate from. Furthermore, when the rEBUS transducer is located close to the presumed location of the target lesion, this confidence reference can also apply to the lesion as it is also presumed moving in a similar fashion.

This confidence reference can be calculated for numerous locations of the rEBUS transducer, and if these historical locations are collected, they can be combined and augmented on the fluoroscopy display to provide an overall confidence reference for the route taken as demonstrated in the dotted region outlining the rEBUS pathway to its left and right Furthermore, tracking in 3D of the radio-opaque profile of the catheter and registering it with either the pre-planned pathway or latest cone beam CT constructed position/updated pathway, can provide the operator with guidance in real time on how to spatially steer the catheter in real time and/or result in a newly constructed calculated pathway in order to arrive at the target lesion with maximal confidence and minimal cone beam CT scans.

In the interventional radiology room, normal clinical procedures including team briefing and debriefing and time-out procedures is followed. The patient is placed onto the scanning bed and sedation is started following standard of care. Routine bronchoscopic evaluation of the central airways will be performed in all cases.

Flexible video bronchoscopes in combination with dedicated video processor can be used during procedures for guiding the navigational and other consecutive tools, such as a brush, TBNA and or biopsy forceps. Introduction of the bronchoscope can be through the mouth, laryngeal mask or endotracheal tube into the bronchial tree. Navigation may be performed on basis of pulmonary physician pre-operative CT-scan knowledge, videoscopic imaging provided by the bronchoscope and real-time fluoroscopic imaging as provided by cone beam CT. If visualization by rEBUS is found possible and confirmed, further steps are consecutively performed. When confirmation of adequate tissue sample is provided, additional tissue samples for cytopathology and molecular analysis can be collected, after which the procedure can be terminated. If it shows that the target lesion is not reached, a switch to the navigation techniques and dedicated tools is made. A preceding cbCT scan will be used for calibration of the navigation technology, to prevent radiation as much as possible.

In subjects with a PPL without bronchus sign or beyond generation 3-4 we will directly start navigation with dedicated tools. When targeting a peripheral pulmonary lesion, the pulmonary physician can use a steerable or non-steerable catheter or tool as inserted through the endoscope's working channel for navigation. Live updates on 3D position may be provided by intermittent 2D fluoroscopy. The fluoroscopy images can be recombined in real time with a CT scan 3D volume made earlier using image fusion and image processing, providing updates on catheter and lesion position. After reaching the target by following the reconstructed pathway as visualized on screen, the probe can be inserted into the catheter (that has been inserted through the endoscope's working channel) for visualization confirmation.

If the peripheral pulmonary lesion shows visible on the probe's images and access of the biopsy forceps/tools inside the target is indeed confirmed, tissue samples can be obtained. Imaging confirmation can be fluoroscopy based, for example. If the peripheral pulmonary lesion does not show visible on the probe's image and/or seems misaligned, repositioning of the catheter is performed and navigation accuracy and probe visualization can be re-assessed.

When the target seems to be reached, repeated tissue biopsy may be performed, and yield may be evaluated.

As an example, during navigation from central to distal, navigation at bifurcations may be cumbersome, since videoscopic imaging may not be able to give positioning information, as one does not know when to make an angulation and in which direction. However, due to the confidence reference, or confidence indicator, provided on the display, the operator is provided with information supportive for the navigation. The confidence reference thus compensates for 4D tissue motion induced by cardiovascular and respiratory movement.

Further, the probe, e.g. a rEBUS probe, does not always provide a clear and unambiguous view of the lesion even though it should be visualized due to the localization of the peripheral pulmonary lesions in the parenchyma without direct contact with the bronchial tree which need to be accessed using transbronchial and transparenchymal access under cone beam CT 3D-guidance, since there is no tissue interface for ultrasound. There may also be a technical limitation in current ultrasound designs, being that it only images radially. Often this gives troubles when the bronchus is ending in the lesion. Another aspect is the lack of tissue contrast for ultrasound in case of so-called ground glass opacities, which are an increasing part of the peripheral pulmonary lesion problem.

A further advantage is provided concerning the 3D distal tip orientation. When navigating it is often unclear to the physician if insertion of tools leads to a 1:1 translation in tissue. As an example, out of plane movement may be poorly visualized. In addition to the orientation, also how the angulation/orientation relates to bronchus bifurcations/the lesion is thus provided.

Once the lesion has been reached and confirmed, repeated biopsy may be provided. As lesion sizing might be as small as 5 mm and tools not positioned directly inside the lesion but only adjacent to the lesion, exact positioning is important. The confidence reference compensates for a lack of knowledge regarding the exact lesion positioning and angulation to the catheter, as it not visible on fluoroscopy, and repeated cone beam CT is not viable, e.g. may be not preferred to provide in view of adding to radiation dose of subject and also staff members. The confidence reference thus also helps in view of the attempt to avoid to systematically biopsy repeatedly around the area of interest if not really needed.

Tracking of the catheter can be provided in an automatic manner. The tracking may thus provide an assessment of both direction and magnitude of cardiovascular and respiratory induced motion by tracking a rEBUS catheter movement continuously when the catheter is left stationary. Preferably, the catheter should be placed near to the lesion or at an approximated pathway that should be taken. Under fluoroscopy, one respiratory (and thus several cardiac cycles) should be monitored. This motion can be modelled and augmented on the fluoroscopy display as confidence references which can be utilized to improve rEBUS catheter navigation to the lesion and provide further information in what region around the target lesion to perform biopsy in, as the lesion is also continuously moving.

In an example, it is further contributed to rEBUS catheter navigation. As a further option, also target lesion location verification and biopsy extraction process is provided while circumventing additional X-ray exposures, like cone beam CT, by augmenting on fluoroscopy the spatial positions visited by the rEBUS catheter and registering them with the pre-procedural CT planning and/or cone beam CT scans and/or electromagnetic navigation.

Furthermore, automatic tracking of a radio-opaque catheter profile enables more feedback to the operator. For example, by tracking multiple markers with known position, with prior knowledge on previous positions during the procedure, it becomes possible to give immediate feedback on 3D positioning, which the operator might intuitively miss otherwise.

In an example, real-time ultrasound visualization of the lesion and position confirmation and biopsy extraction are facilitated if e.g. a tracked catheter is combined with a biopsy extracting mechanism.

In an example, a catheter is provided that is able to guide a 're-entry' needle. This can be used in the same fashion as in an EBUS transbronchial needle aspiration (TBNA), which is a staging procedure, for puncturing the lesion and consecutive guidance of a guidewire into that lesion. A secondary step would then be to guide a needle over that guidewire into the lesion directly, giving an improved local confirmation of accurate tissue biopsy. For example, an accuracy of nearly up to 100% is achievable.

According to an aspect, potential and/or existing catheter radio-opaque properties are used for automated tracking under fluoroscopy in bronchoscopy navigation for enhancing rEBUS catheter navigation to the lesion, lesion confirmation and biopsy extraction. For example, computer vision and image processing for 2D and/or 3D tracking of the catheter is deployed. Further, it is provided to augment fluoroscopy images and to display with the results of catheter tracking in 2D and/or 3D. In another example, results of catheter tracking in 2D/3D are registered with results of pre-procedural CT planning and/or cone beam CT scans and/or electromagnetic navigation.

Automated rEBUS tracking is provided, e.g. as an endobronchial navigational software package. The results are visible on the display.

The provision of the confidence reference is provided, as example, to enhance existing cone beam CT system functionality and also to provide improvement in the field of lung inspection and treatment, e.g. for endo bronchial navigation. The catheter tracking with rEBUS resulting in the confidence reference is provided to enhance fluoroscopy augmented display further. As a further option, results of rEBUS catheter tracking are registered with existing calculated and displayed pathways, e.g. either pre-operative and/or achieved via intra operative cone beam CT scans. A still further option is to enhance spatial/3D navigation of the rEBUS catheter by further integration with cone beam CT. The provision of the confidence reference also improves bronchial usage of disposables such as ultrasound catheters and their future variations.

In an example, it is suggested to look at the possibility of how a C-arm sweep in one or multiple angulations can also localize and/or reconstruct in 3D. And further how an intra-operative CBCT can be updated with the model information and vice versa (and with pre-procedural bronchial anatomy segmentation).

Further, in an example, the rEBUS device is integrated with electromagnetic tracking of the device.

In a further example, an adjustment in 2D fluoroscopy imaging angle is provided to provide improved accuracy of the visualized model.

In a further example, operator induced deformation of the lung/devices is distinguished from repetitory respiratory/cardiac motion.

As indicated, a pre-procedural segmentation of a bronchial tree is overlaid on fluoroscopy.

In an option, once rEBUS confirmatory of lesion access is provided, its position information is provided as input to the system such to track where and how the rEBUS is located in the model.

In an example, it is provided to extract global features like bigger vessels. These can be used for updating the model accuracy, e.g. pre-procedural bronchial tree segmentation combined with vessel segmentation, and local deformation.

As an option, an automatic zoom and collimation function is provided for the navigation.

In an example, a computer program enabling a processor to carry out the method of one of the examples above is provided.

In an example, a computer program or program element for controlling an apparatus according to one of the examples above is provided, which program or program element, when being executed by a processing unit, is adapted to perform the method steps of one of the method examples above.

In an example, a computer readable medium having stored the program element of the above example is provided.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit or be distributed over more than one computer units, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

Aspects of the invention may be implemented in a computer program product, which may be a collection of computer program instructions stored on a computer readable storage device which may be executed by a computer. The instructions of the present invention may be in any interpretable or executable code mechanism, including but not limited to scripts, interpretable programs, dynamic link libraries (DLLs) or Java classes. The instructions can be provided as complete executable programs, partial executable programs, as modifications to existing programs (e.g. updates) or extensions for existing programs (e.g. plugins). Moreover, parts of the processing of the present invention may be distributed over multiple computers or processors.

As discussed above, the processing unit, for instance a controller implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims.

However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for facilitating navigation of an intrathoracic device inside a bronchial pathway, the device comprising:
    an image data provider;
    a processor; and
    an output data provider;
    wherein the image data provider is configured to receive a sequence of 2D X-ray images of a region of interest of a bronchial structure with the intrathoracic device inserted in the bronchial pathway; wherein the intrathoracic device is visible in the 2D X-ray images;
    wherein the processor is configured to track the intrathoracic device in at least a part of the sequence of 2D X-ray images; and to assess direction and magnitude of repetitory cardiovascular and respiratory induced motion based on the tracked intrathoracic device; and to model the assessed motion and generate a navigation information indicative of a range of the modelled motion; and
    wherein the output data provider is configured to provide the navigation information as a confidence reference to a user operating the intrathoracic device.

2. The device according to claim 1, wherein the confidence reference is provided as an indication of an envelope enclosing the range of the modelled motion.

3. The device according to claim 1, wherein the output data provider comprises a display that is configured to display the confidence reference overlaid to a current one of the sequence of 2D X-ray images.

4. The device according to claim 1, wherein the processor is configured to track the intrathoracic device in at least a part of the sequence of 2D X-ray images; and to assess direction and magnitude of non-repetitory lung tissue and device motion as induced by intrathoracic device manipulation or guiding elements of the intrathoracic device; and to track the non-repetitory motion and generate a navigation information which is adjusted for the non-repetitory motion.

5. The device according to claim 1,
    wherein the image data provider is further configured to provide pre-operative 3D image data comprising a segmented bronchial structure of a subject in the region of interest;
    wherein the processor is configured to register the 2D X-ray images with the pre-operative 3D image data; and to determine a spatial position of the intrathoracic device in relation to the segmented bronchial structure of the pre-operative 3D image data based on 2D X-ray projection of the intrathoracic device; and
    wherein the output data provider comprises a display that is configured to display the confidence reference in a projection of the segmented bronchial structure, which are both overlaid to a current one of the sequence of 2D X-ray images.

6. The device according to claim 5, wherein the image data provider is further configured to provide 3D image data originating from intra operative X-ray fluoroscopy and the device further comprising a segmented bronchial structure of the subject in the region of interest;
    wherein the processor is configured to register the 2D X-ray images with the 3D image data; and to determine a spatial position of the intrathoracic device in relation to the segmented bronchial structure of the 3D image data based on the 2D X-ray projection of the intrathoracic device; and
    wherein the output data provider comprises a display that is configured to display the confidence reference overlaid in 3D form on the display of the 3D image data.

7. The device according to claim 1, wherein the image data provider is configured to receive, as the sequence, a live stream of 2D X-ray images; and
    wherein the processor is configured to continuously track the intrathoracic device in the live stream of 2D X-ray images; and to update the navigation information accordingly; and
    wherein the output data provider is configured to continuously provide the navigation information as an updated confidence reference to a user operating the intrathoracic device.

8. The device according to claim 1, wherein the navigation information is at least one of further updated and integrated with electromagnetic tracking information.

9. A system for navigation of an intrathoracic device inside a bronchial pathway, the system comprising:
- an X-ray imaging device for imaging a thorax area of interest of a subject;
- the intrathoracic device for insertion in the bronchial pathway of the subject;
- a display;
- a device for facilitating navigation according to claim 1; and
- wherein the intrathoracic device is at least partly radio-opaque;
- wherein the X-ray imaging device provides a sequence of 2D X-ray images of a region of interest of a bronchial structure with the intrathoracic device inserted in the bronchial pathway;
- wherein the device for facilitating navigation provides navigation information to the display; and
- wherein the display provides at least one of the sequence of the 2D X-ray images and the navigation information as a confidence reference overlaid to the 2D X-ray images.

10. The system according to claim 9, wherein the intrathoracic device is an ultrasound imaging probe configured to provide radial endobronchial ultrasonography data from within the bronchial structure.

11. The system according to claim 9, wherein the radial endobronchial ultrasonography data from within the bronchial structure is visualized and also shown on the display.

12. The system according to claim 9, wherein the intrathoracic device comprises an ultrasound imaging probe and a biopsy extraction device.

13. A method for navigation of an intrathoracic device inside a bronchial pathway, the method comprising:
- receiving a sequence of live 2D X-ray images of the region of interest of a bronchial structure with the intrathoracic device inserted in the bronchial pathway; wherein the intrathoracic device is visible in the live 2D X-ray images;
- tracking the intrathoracic device in at least a part of the sequence of live 2D X-ray images;
- assessing direction and magnitude of repetitory cardiovascular and respiratory induced motion based on the tracked intrathoracic device;
- modeling the assessed motion and generating navigation information indicative of the modelled motion; and
- providing the navigation information as a confidence reference to a user operating the intrathoracic device.

14. A computer program enabling a processor to carry out the method of claim 13.

15. A non-transitory computer readable medium having stored the computer program of claim 14.

* * * * *